(12) United States Patent
Davidson et al.

(10) Patent No.: US 6,319,379 B1
(45) Date of Patent: Nov. 20, 2001

(54) MODIFIED ELECTROKINETIC SAMPLE INJECTION METHOD IN CHROMATOGRAPHY AND ELECTROPHORESIS ANALYSIS

(75) Inventors: J. Courtney Davidson; Joseph W. Balch, both of Livermore, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/379,378

(22) Filed: Aug. 23, 1999

(51) Int. Cl.[7] .................................................. G01N 27/26
(52) U.S. Cl. ............................................ 204/453; 204/451
(58) Field of Search ..................................... 204/451, 453, 204/601, 604

Primary Examiner—Jill Warden
Assistant Examiner—Alex Noguerola

(74) Attorney, Agent, or Firm—L. E. Carnahan; Alan H. Thompson

(57) ABSTRACT

A sample injection method for horizontal configured multiple chromatography or electrophoresis units, each containing a number of separation/analysis channels, that enables efficient introduction of analyte samples. This method for loading when taken in conjunction with horizontal microchannels allows much reduced sample volumes and a means of sample stacking to greatly reduce the concentration of the sample. This reduction in the amount of sample can lead to great cost savings in sample preparation, particularly in massively parallel applications such as DNA sequencing. The essence of this method is in preparation of the input of the separation channel, the physical sample introduction, and subsequent removal of excess material. By this method, sample volumes of 100 nanoliter to 2 microliters have been used successfully, compared to the typical 5 microliters of sample required by the prior separation/analysis method.

20 Claims, 2 Drawing Sheets

MODIFIED ELECTROKINETIC SAMPLE INJECTION METHOD IN CHROMATOGRAPHY AND ELECTROPHORESIS ANALYSIS

The United States Government has rights in this invention pursuant to Contract No. W-7405-ENG-48 between the United States Department of Energy and the University of California for the operation of Lawrence Livermore National Laboratory.

BACKGROUND OF THE INVENTION

The present invention relates to chromatography and electrophoresis analysis, particularly to a method of sample injection into a number of horizontal separation/analysis channels, and more particularly to an improved method that enables the efficient introduction of analyte samples wherein the amount of sample is significantly reduced and a means of sample stacking is provided.

Chromatography and electrophoresis analysis systems use columns filled with various media to separate analytes based on differing analyte mobilities due to an applied electric field. In all cases the introduction of sample is paramount to achieving quality results. Specifically, samples containing multiple analytes must be introduced in a tight zone to achieve high separation resolution. Discrete capillary systems have addressed this issue by using a time gated electrokinetic injection process whereby the lead end of the capillary is suspended vertically into a sample vial that contains the sample resuspended in a loading buffer. An electrode is placed into the loading buffer and a potential is applied on the order of seconds to drive the sample into the capillary. Typically it takes on the order of 5 microliters of sample solution to permit the required electrical contact to drive the sample. Once the sample has been introduced, the capillary is removed from the sample loading buffer and placed in a running buffer for the extent of the analysis. Due to the high costs of sample preparation, particularly in massively parallel applications such as DNA sequencing, there has been a need to reduce the amount of sample solution required to inject a small amount of sample into the separation/analysis channels.

The present invention provides a method for reducing the typical use of 5 microliters of sample solution to an amount of under 0.2 microliters, thus providing a great cost savings in sample preparation. Basically, the method of the present invention comprises a modified electrokinetic sample injection procedure, which involves preparation of the input of the separation channel, the physical sample introduction, and subsequent removal of excess material. This method is very useful for high throughput analysis systems such as DNA sequencing, and it will enable uniquely controllable sample stacking for increased loading efficiency electrophoresis.

SUMMARY OF THE INVENTION

It is an object of the present invention to provide a modified electrokinetic sample injection method for chromatography and electrophoresis analysis systems.

A further object of the invention is to provide an improved method for loading horizontal separation/analysis channels.

A further object of the invention is to reduce the quantity of sample solution used in horizontal microchannel separation/analysis systems.

Another object of the invention is to provide a method for loading when taken in conjunction with horizontal microchannel which allows much reduced sample volumes.

Another object of the invention is to provide a method for loading samples which provides a means of sample stacking to greatly reduce the concentration of the sample.

Another object of the invention is to provide a modified electrokinetic sample injection method which greatly reduces the amount of sample required for separation/analysis and the associated cost savings in sample preparation.

Other objects and advantages of the present invention will become apparent from the following description and accompanying drawings. The essence of the present invention is in the preparation of the input of the separation channel, the physical sample introduction, and subsequent removal of excess material. The invention is a modified electrokinetic sample injection method for chromatography and electrophoresis analysis, wherein the amount of sample volume is significantly reduced (i.e. 5 $\mu$liters down to ~0.2 $\mu$liters). By the reduction of the amount of sample used for analysis systems incorporating multiple horizontal microchannels, the cost of sample preparation is greatly reduced, which is significant in massively applications such as DNA sequencing. Basically the method of this invention involves: (1) filling the microchannels with separation media, (2) removal of the media from the input sample load well, (3) loading the sample resuspended in a high density buffer, (4) applying an electric field to load sample into the separation media, (5) removing the electric field and decanting excess sample, and (6) applying separation electric field for analysis.

BRIEF DESCRIPTION OF THE DRAWINGS

The accompanying drawings, which are incorporated into and form a part of the disclosure, illustrate an embodiment of an apparatus and the method of the invention and, together with the description, serve to explain the principles of the invention.

DETAILED DESCRIPTION OF THE INVENTION

The present invention is a modified electrokinetic sample injection method for chromatography and electrophoresis analysis. The method of this invention involves loading sample in horizontal microchannels which allows much reduced sample volumes and a means of sample stacking to greatly reduce the concentration of the sample. This reduction in the amount of sample volume (typically 5 $\mu$liters) to a range of 100 nanoliter to 2 $\mu$liters leads to a great cost savings in sample preparation, particularly in massively parallel applications such as DNA sequencing.

The essence of the present invention involves preparation of the input of the separation channel, the physical sample introduction, and subsequent removal of excess material. The method is carried out using glass microchannels for separation columns. These microchannels are confined between two pieces of glass. Specifically, one piece of glass, a microchannel plate, has channels etched into its surface. A top or cover plate of glass is bonded to the microchannel plate. The top plate has holes in it that match up to the ends of each microchannel. These holes range in size for 0.5 to 1 mm in diameter and are nominally 1 to 5 mm deep. Each microchannel is independently addressed at each end by these holes. The sample load end of the plates is surrounded by a reservoir containing a buffer material.

Figure 1:
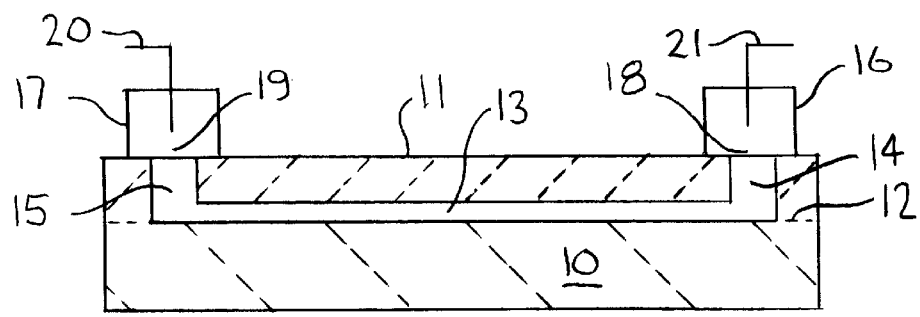
FIG. 1 schematically illustrates a horizontal microchannel and input/output reservoir of a typical analysis system.

FIG. 1 schematically illustrates a typical separation column as described above, and includes a glass substrate or microchannel plate 10 and a top plate 11, bonding together as indicated at dotted line 12. The plate 11 includes one or more microchannels 13, and the plate 11 includes one or more input and output holes 14 and 15, which are in fluid communication with each end of microchannel(s) 13, as described above. An input buffer reservoir 16 is mounted adjacent hole(s) 14, and an output reservoir 17 is mounted adjacent hole(s) 15. The hole(s) 14 functions a sample load well indicated at 18 and the hole(s) 15 function as discharge wells indicated at 19. Electrodes 20 and 21 are mounted in each of reservoirs 16 and 17, respectively, and are connected to a controlled electrical power supply not shown, but known in the art, for producing an electric field through separation medium contained in said microchannel(s) 13, as described hereinafter.

Figure 2:
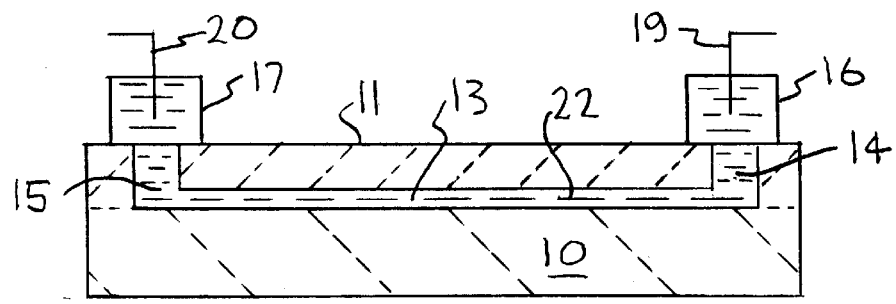
FIGS. 2–7 illustrate the sequence of operation for carrying out the method of the present invention.
Figure 3:
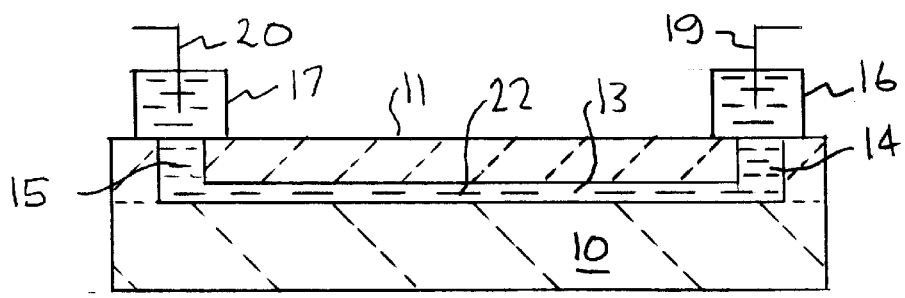
Figure 4:
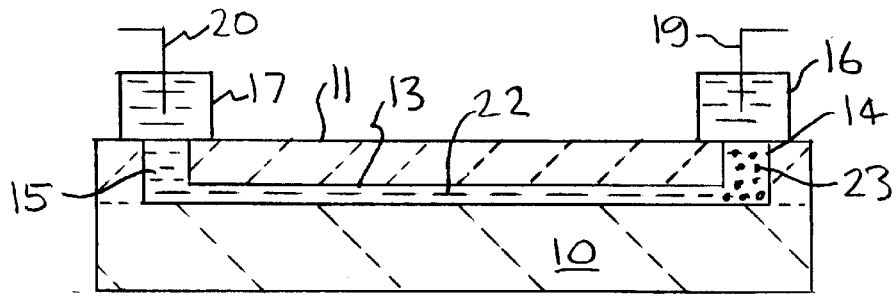
Figure 5:
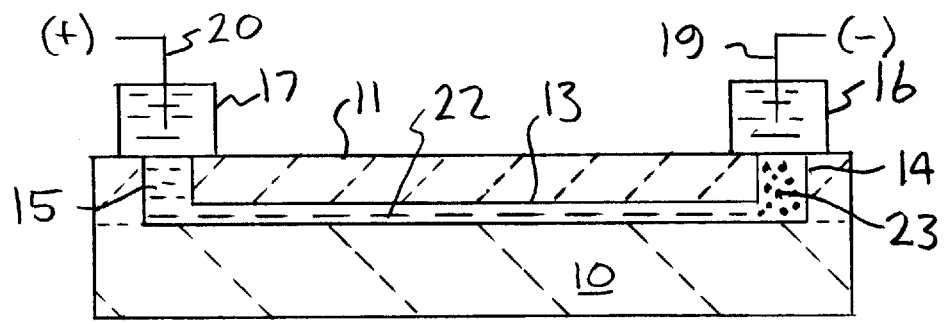
Figure 6:
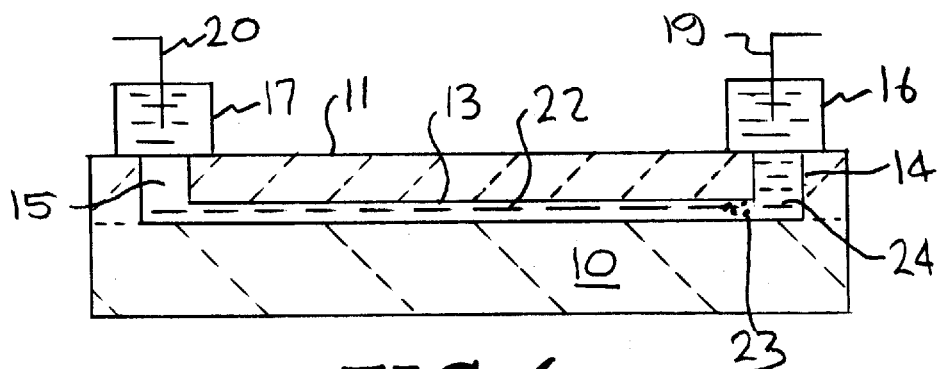
Figure 7:
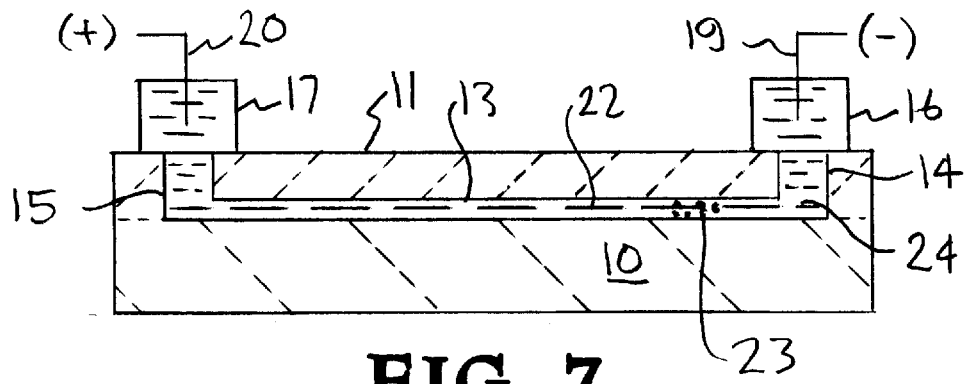

The method of this invention begins by the input buffer reservoir 16 being filled with water or a loading buffer material. A separation media or medium 22, see FIG. 2, is introduced into microchannel 13 via reservoir 17 and hole 15 at the other end so as to fill the entire channel 13 and the input and output holes 14 and 15. Once the channel 13 has been filled with the separation media 22, the output reservoir 17 is filled with material, such as sieving media or running buffer the separation media is suctioned out of the input (sample load) hole 14, as by vacuum, see FIG. 3. This preparation step or operation can also be carried out by blowing the separation media out with a liquid stream. The purpose of this step or operation is to obtain a minimal separation media cross sectional area as established by the dimensions of the microchannel, which is on the order of a few hundred microns wide by 50 microns deep. This cleanout step or operation is done in this submarine fashion to assure that the separation media that is removed is replaced with a bubble free liquid. With the separation media removed from input load well 18 (which includes hole 14 and an adjacent end of microchannel 13 (see FIG. 3), sample 23 resuspended in a high density loading buffer are introduced into the hole 14 (sample load well 18), as shown in FIG. 4. Sample volumes of 100 nanoliter to 2 microliters have been demonstrated to work successfully. The smaller (nanoliter) amounts represent a significant reduction in the sample volumes (typically 5 microliters) used in more conventional capillary and slab gel electophoresis systems. The high density buffer, such as formamide, ficol, or dextran, allows the sample 23 to sink to the bottom of the sample load well 18 (hole 14) and come into intimate contact with the separation media 22 interface. In this way the applied electrical field, see FIG. 5, is dropped directly across the sample 23 thus optimizing the transfer of sample 23 onto the separation media 22. Once the sample 23 has been introduced into the well 18, the electric field (strength of 50 V/cm to 160 V/cm) formed between electrodes 19 and 20 via separation media 22 is applied, see FIG. 5, for a prescribed length of time typically on the order of seconds to 10's of seconds. Variations in sample loading field strength and time of injection are optimized for the separation of interest. After the sample 23 has been momentarily driven into the separation media 22, as seen in FIG. 5, the electric field is turned off and the excess sample is siphoned off, see FIG. 6, using a pipette tip uptake of 50 to 100 microliters of liquid. In this step or operation, the excess sample is swept out of the input hole 14 (load well 18) by the liquid 24 contained in the reservoir 16, i.e., either water or running buffer. Upon removal of the excess sample 23, the application of the electric field is resumed, see FIG. 7, for the duration of the separation analysis period, whereby the sample 23 is driven along the microchannel 13 towards output hole 15 (discharge well 20), as shown in FIG. 7 and as known in the art. Post loading field strengths are optimized to achieve the best resolution performance. A lower applied field (strength of 50 V/cm to 80 V/cm) on the order of one-half the driving field ( strength of 100 V/cm to 160 V/cm) for a few (one to three) minutes prior to the application of the full drive field strength has been proven beneficial.

It has thus been shown that the present invention provides an improved method for chromatography and electrophoresis analysis. The improved method involves a modification of prior electrokinetic sample injection methods and enables the efficient introduction of analyte samples for multiple chromatography or electropheresis units each containing a number of separation/analysis channels, especially those in a horizontal configuration. This method will be useful for high throughput analysis systems such as DNA sequencing. It will enable uniquely controllable sample stacking for increased loading efficiency electrophoresis. Also, it can be used in the analysis of biological materials for drug discovery effects, genetic disease susceptibility diagnostics and studies. By the use of the present invention the sample volume required for analysis is significantly less (up to approximately 40 times less) thus greatly reducing the costs of sample preparation.

While a specific sequence of operational procedures has been set forth, with specified materials and parameters, to exemplify and teach the principles of the invention, such are not intended to be limiting. Modifications and changes may become apparent to those skilled in the art, and it is intended that the invention be limited only by the scope of the appended claims.

What is claimed is:

1. In a method of electrokinetic sample injection in chromatography and electrophoresis analysis using a microchannel apparatus comprising at least one microchannel and at least one sample load well, the improvement including:

filling the at least one microchannel with a separation media, removing the separation media from the at least a sample load well, loading sample in the sample load well, applying an electric field to load sample into the separation media, removing the electric field, removing excess sample from the load well, and applying an electric field through the separation media for analysis of the sample load into the separation media.

2. The improvement of claim 1, additionally including filling an input reservoir adjacent the sample load well prior to filling the at least one microchannel with separation medium.

3. The improvement of claim 2, wherein the input reservoir is filled with water or a loading buffer.

4. The improvement of claim 1, wherein filling the at least one microchannel with the separation medium is carried out by directing the separation media through at least an output opening located at an end of the microchannel opposite the sample load well.

5. The improvement of claim 4, wherein the separation media also fills the sample load well and the output opening.

6. The improvement of claim 1, wherein removing separation media from at least the sample load well is carried out by suction or by blowing with a liquid stream.

7. The improvement of claim 1, wherein the loaded sample comprises sample resuspended in a high density loading buffer.

8. The improvement of claim 1, wherein applying the electric field to load sample onto the separation media is carried out in a length of time on the order of seconds to 10's of seconds.

9. The improvement of claim 1, wherein removing excess sample from the load well is carried out by siphoning.

10. The improvement of claim 9, wherein the siphoning is carried out using a pipette tip uptake of 50 to 100 microliters of liquid.

11. The improvement of claim 9, wherein excess sample is swept out of the input load well by liquid contained in an input reservoir.

12. The improvement of claim 1, wherein the electric field when applied for analysis of the sample is lower for a time period prior to an application of a full strength drive electric field.

13. The improvement of claim 1, wherein the lower electric field is about ¼ to ½ the drive electric field and the time period is on the order of 1 to 3 minutes.

14. A modified electrokinetic sample injection method for use in chromatography and electrophoresis analysis using a microchannel apparatus having at least one microchannel intermediate an input opening and an output opening, and having an input reservoir and an output reservoir located adjacent the input and output openings, including:

filling the input reservoir with water or a loading buffer, introducing a separation medium into the at least one microchannel via the output opening until the input opening, the microchannel, and the output opening are filled, removing the separation medium from at least the input opening to obtain a minimal media cross-sectional area, introducing sample resuspended in a high density buffer into the inlet hole and in contact with the separation medium, applying an electric field across the separation medium and the sample to transfer sample onto the separation medium, removing the electric field and excess sample, and reapplying the electric field across the separation medium and sample for driving the sample through the microchannel for analysis.

15. The method of claim 14, wherein removing the separation medium from at least the input opening is carried out by suction or by blowing with a liquid stream.

16. The method of claim 14, wherein removing the separation medium is carried out by a submerged technique to assure that the medium removed is replaced with a bubble free liquid.

17. The method of claim 14, wherein the first-mentioned electric field is applied for a time period of 1 to 10's of seconds.

18. The method of claim 14, wherein removing the excess sample is carried out siphoned off or swept out of the input hole by liquid contained in the input reservoir.

19. The method of claim 14, wherein reapplying the electric field is carried out for a time period at a lower field strength, and then at a full field strength.

20. The method of claim 19, wherein the lower field strength is about one-half the full field strength.

* * * * *